United States Patent
Mukai

[19]

[11] Patent Number: 5,971,978
[45] Date of Patent: Oct. 26, 1999

[54] LASER TREATMENT APPARATUS

[75] Inventor: Hideo Mukai, Toyohashi, Japan

[73] Assignee: Nidek Co., Ltd., Japan

[21] Appl. No.: 09/132,236

[22] Filed: Aug. 11, 1998

[30] Foreign Application Priority Data

Aug. 29, 1997 [JP] Japan .................................. 9-249400

[51] Int. Cl.[6] ................................................. A61B 17/36
[52] U.S. Cl. ............................................. 606/18; 606/11
[58] Field of Search .................. 606/4, 5, 6, 10, 606/11, 12, 15, 16, 17, 18

[56] References Cited

U.S. PATENT DOCUMENTS

| | | | |
|---|---|---|---|
| 4,579,430 | 4/1986 | Bille | 606/4 |
| 4,887,019 | 12/1989 | Reis et al. | 606/4 X |
| 5,049,147 | 9/1991 | Danor | 606/10 |
| 5,336,217 | 8/1994 | Buys et al. | 606/9 |
| 5,411,502 | 5/1995 | Zair | 606/10 |
| 5,514,127 | 5/1996 | Shanks | 606/10 |
| 5,533,997 | 7/1996 | Ruiz | 606/5 |
| 5,546,214 | 8/1996 | Black et al. | 359/203 |
| 5,645,550 | 7/1997 | Hohla | 606/108 |
| 5,743,902 | 4/1998 | Trost | 606/18 |

FOREIGN PATENT DOCUMENTS

| | | |
|---|---|---|
| 0 151 869 | 8/1985 | European Pat. Off. . |
| 3837 248 A1 | 5/1990 | Germany . |
| WO 97/19725 | 6/1997 | WIPO . |

OTHER PUBLICATIONS

European Search Report dated Dec. 11, 1998.

Communication dated Dec. 21, 1998.

*Primary Examiner*—Linda C. M. Dvorak
*Assistant Examiner*—Sonya Harris
*Attorney, Agent, or Firm*—Finnegan, Henderson, Farabow, Garrett & Dunner, L.L.P.

[57] ABSTRACT

A laser treatment apparatus which irradiates a laser beam produced by a treatment laser source to an area of treatment, the apparatus comprises an irradiation condition setting device which sets irradiation conditions of the laser beam, such as an irradiation area, a laser scanning device provided with a plurality of reflectors including at least a reflector which is continuously rotated in a predetermined direction by a motor to perform a laser two-dimensional scanning on the treatment area, a scanning controller which controls the operation of the laser scanning device, and an irradiation controller which controls the laser source to turn on and off the laser beam depending on the irradiation conditions in correspondence with the operation of the laser scanning device.

6 Claims, 8 Drawing Sheets

PRIOR ART

FIG. 8 (b)

LASER TREATMENT APPARATUS

BACKGROUND OF THE INVENTION

1. Field of the Invention

The present invention relates to a laser treatment apparatus which is used to treat a patient by irradiating a laser beam to a part of body to be treated (diseased part).

2. Description of Related Art

Laser treatment apparatus for treating a part of a patient's body to be treated (diseased part) by irradiating a laser beam thereto has been used for the treatment of various diseases based on the selection of the wavelength of treatment laser.

In the recent neoplasty for removing wrinkles, ephelides, birthmarks, stains, etc. of patients, attention is paid to laser treatment apparatus that use the $CO_2$ laser (carbon dioxide gas laser) having infrared wavelengths. In the neoplasty using these laser treatment apparatus, a treatment laser beam is irradiated through a hand piece to the diseased part of a patient. For one of the laser treatment apparatus, there is an apparatus provided with the hand piece having driven mirrors which deflect a treatment laser beam and an aiming light to scan the diseased part in the X-direction and the Y-direction respectively.

However, the driven mirrors for the X- and Y-directions in the conventional laser treatment apparatus are swinging mirrors such as galvano-mirrors, which will change its moving speed according to swinging angle. Consequently, the mirror in moving slowly causes the over-irradiation of the treatment laser beam onto the part to be treated.

SUMMARY OF THE INVENTION

The present invention has been made in view of the above circumstances and has an object to overcome the above problems and to provide a laser treatment apparatus which enables the appropriate treatment with a laser beam of a constant energy density in a laser scanning area, thus preventing the over-irradiation of a treatment laser beam onto a part to be treated.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, there is provided a laser treatment apparatus which irradiates a laser beam produced by a treatment laser source to an area of treatment, the apparatus comprising irradiation condition setting means for setting irradiation conditions of the laser beam, including an irradiation area, laser scanning means which is provided with a plurality of reflectors including at least a reflector which is continuously rotated in a predetermined direction by a motor, and which performs a laser two-dimensional scanning on the treatment area, scanning control means which controls an operation of the laser scanning means, and irradiation control means which controls the laser source to turn on and off the laser beam depending on the irradiation conditions in correspondence with an operation of the laser scanning means.

According to the present invention, an appropriate laser treatment can be implemented without the over-irradiation of a treatment laser beam.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention. In the drawings.

FIG. 8(*a*) is a graph used to explain the scanning manner of the treatment laser beam in a prior art; and FIG. 8(*b*) is a graph used to explain the scanning manner of the treatment laser beam in the present invention.

DETAILED DESCRIPTION OF THE PREFERRED EMBODIMENTS

Figure 1:
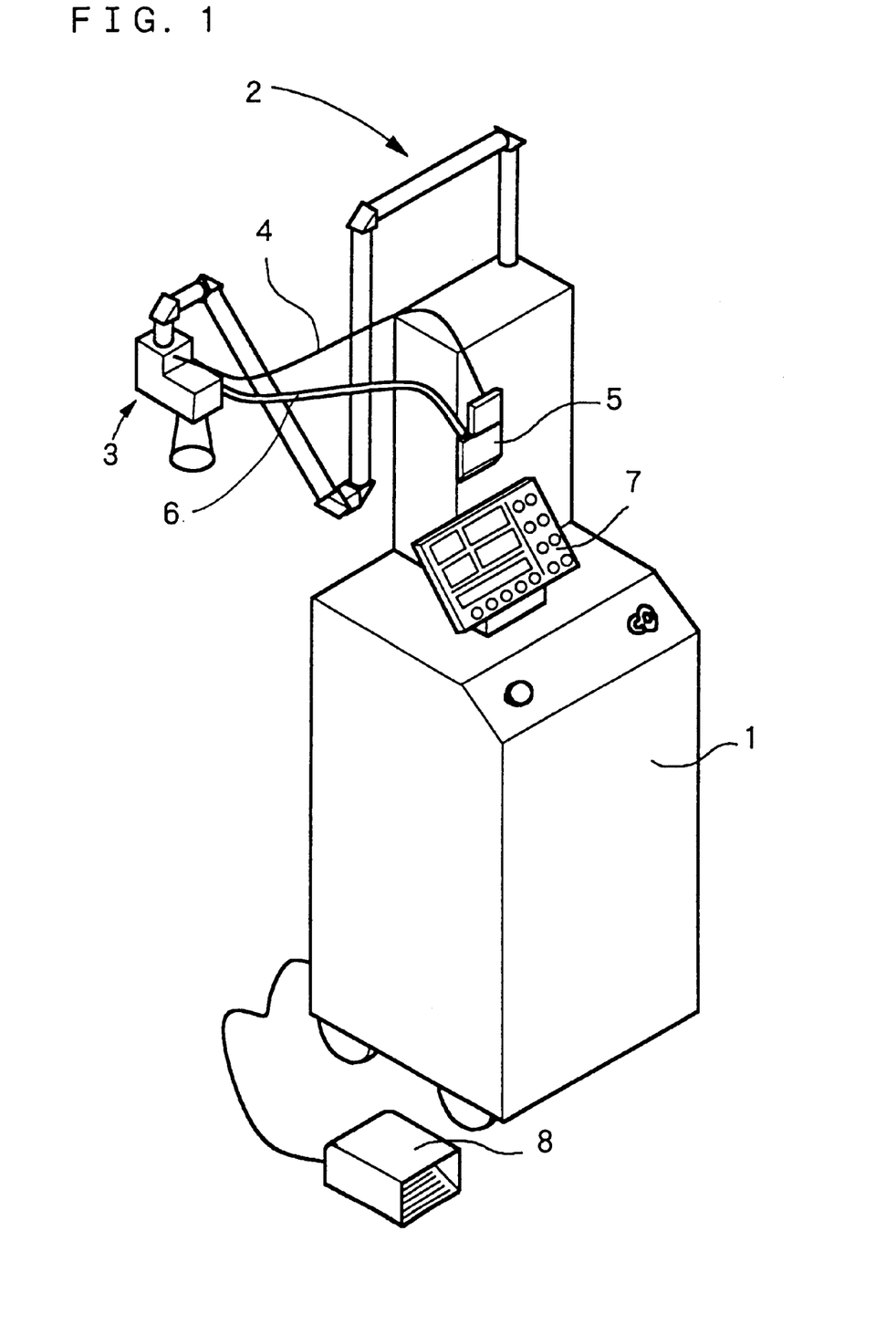
FIG. 1 is a schematic diagram of the laser treatment apparatus in an embodiment according to the present invention.

A detailed description of preferred embodiments of a laser treatment apparatus embodying the present invention will now be given referring to the accompanying drawings. FIG. 1 schematically shows the external view of the laser treatment apparatus in the present embodiment.

The apparatus includes a laser unit 1, which incorporates a treatment laser source, an aiming light source, an optical system, a controller, a scanner controller, and so on. In this embodiment, the treatment laser source is a $CO_2$ laser which emits an infrared laser beam, and the aiming light source is a semiconductor laser which emits a visible red laser beam. The apparatus further includes a multi-joint arm section 2, a hand piece unit 3 which operates to scan a treatment area, a cable 4, a connector 5, an air tube 6, a control panel 7 which is used by an operator to set laser irradiation conditions, etc., and a foot switch 8 which is depressed by the operator to produce a trigger signal. The connector 5 is provided with a microswitch for detecting the connection or disconnection of the cable 4.

The multi-joint arm section 2 is made up of several rigid pipes linked by joints, so that the operator can move in three-dimensional manner the hand piece unit 3 which is attached at the end of the arm section 2. Mirrors are fitted in the joints of the multi-joint arm section 2, so that the treatment laser beam and the aiming light beam that are aligned coaxially with each other in the laser unit 1 are guided to pass through the multi-joint arm section 2 and reach the hand piece unit 3. The hand piece unit 3 is among a variety of detachable units designed to meet individual purposes and usage. In the present embodiment, the apparatus is equipped with a scanning hand piece unit 3 having a scanner head which deflects the laser beam to scan the scanning area of treatment.

Figure 2:
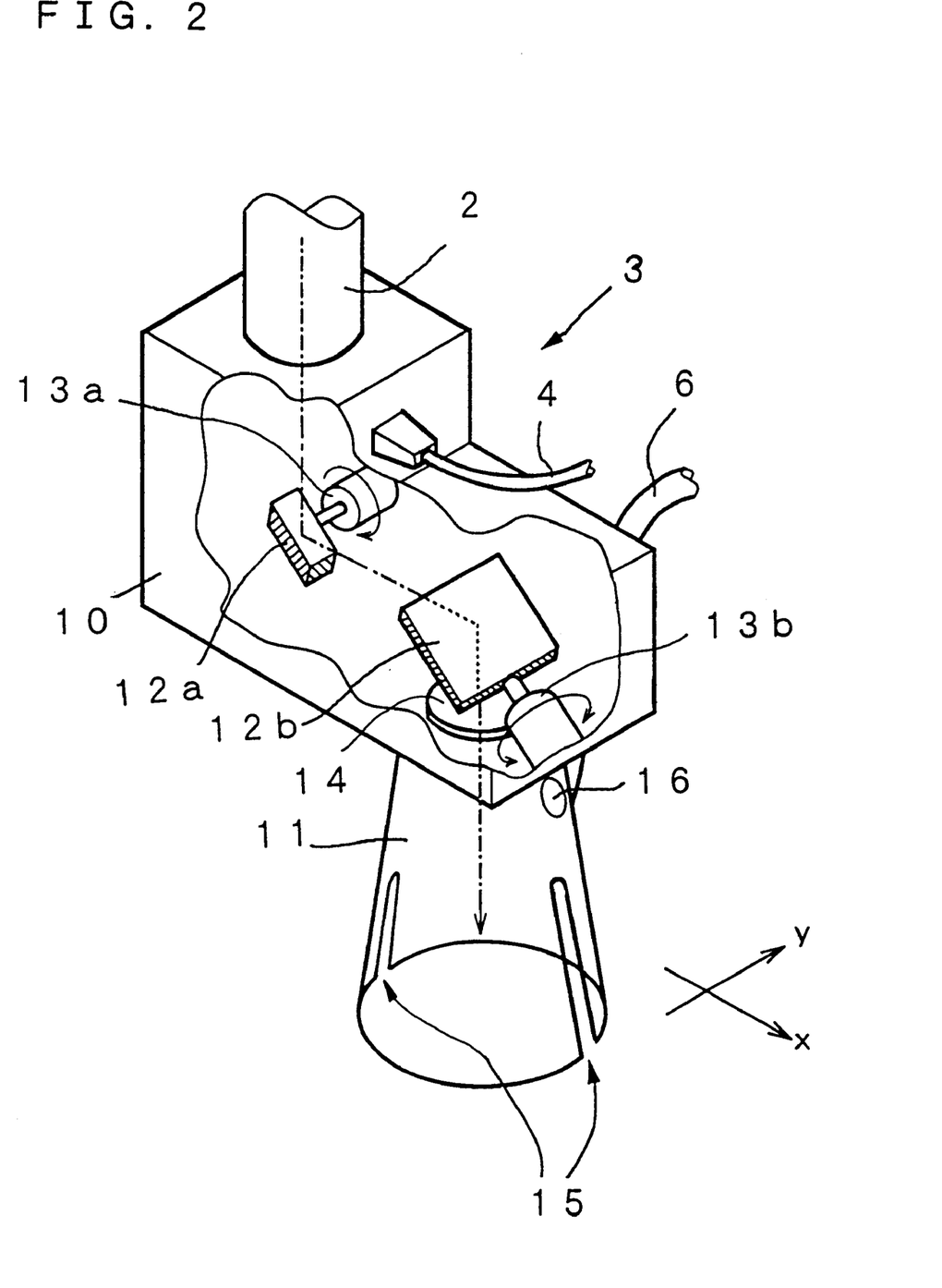
FIG. 2 is a schematic diagram with a partially sectional view of a hand piece unit in the laser treatment apparatus.
Figure 3:
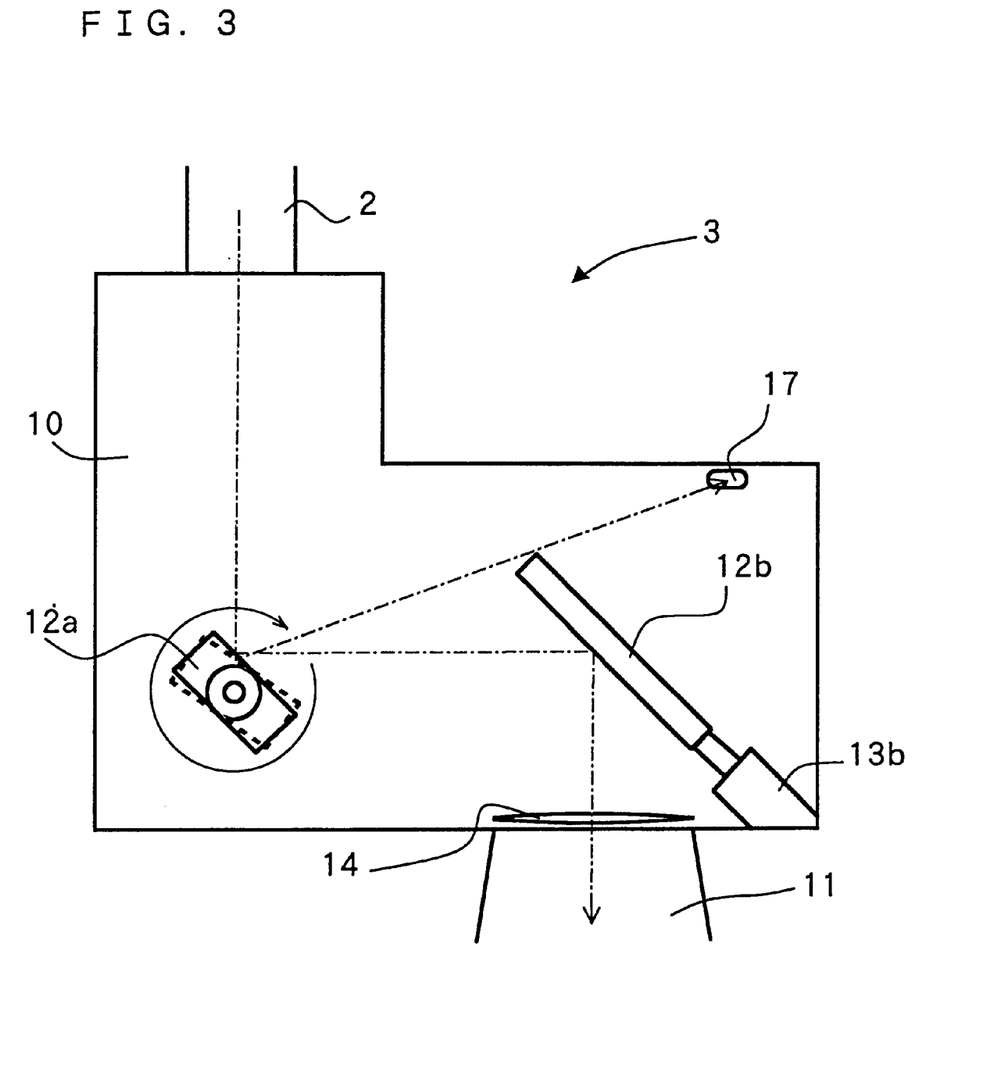
FIG. 3 is a schematic sectional diagram of the hand piece unit.

FIG. 2 is a schematic diagram with a partially sectional view of a hand piece unit. FIG. 3 is a schematic sectional diagram of the same.

The hand piece unit 3 consists of a scanner section 10 and a hand piece head section 11 which are separable. The scanner section 10 incorporates driven mirrors 12*a* and 12*b* which deflect the treatment laser beam and aiming light beam, which have come through the multi-joint arm section 2, to scan the treatment area in two-dimensional manner in the X/Y directions, drive motors 13a and 13b which swing or rotate the mirrors 12a and 12b, a condenser (focusing) lens 14, and a sensor 17.

In the embodiment, the driven mirror 12a for the X-direction is a polygon mirror and the drive motor 13a for rotating the driven mirror 12a is a DC servomotor. With the polygon mirror having a reflecting surface with low surface roughness, non-uniformity in the irradiation density or the irradiation position of the treatment laser beam deflected by the polygon mirror can be reduced. If using the polygon mirror having two or more sides (a two-sided mirror is used in the present embodiment), the rotating speed of the drive motor can be lowered, reducing the generation of heat or noise in the drive motor. On the other hand, a galvano-mirror which consists of a driven mirror and a drive motor incorporated in one body is used for the driven mirror 12b for the Y-direction and the drive motor 13b.

The drive motors 13a and 13b are controlled by the scanner controller in the laser unit 1. The scanner controller produces drive signals, which are fed through the connector 5 and cable 4 to the drive motors 13a and 13b in the scanner section 10, by which the driven mirror 12a is rotated in a predetermined direction at a predetermined speed and the driven mirror 12b is swung to a desired angle at a predetermined step (speed). Alternatively, each of the driven mirrors 12a and 12b may be stopped at a desired angle.

The driven mirror 12a which is thus rotated by the drive motor 13a in a predetermined direction at a predetermined speed is controlled to deflect the treatment laser beam or the aiming light beam toward a desired position (area) on the driven mirror 12b in order to irradiate the irradiation area depending on the irradiation conditions such as the form and size of irradiation area. For the purpose, the scanner section 10 is provided with the sensor 17 which detects the aiming light beam deflected by the driven mirror 12a in the hand piece unit 3. On detecting the aiming light beam, the sensor 17 transmits a signal to the controller, which measures the preset time which has been determined in advance based on the rotating speed and direction of the drive motor 13a and the irradiation conditions.

The controller controls the irradiation of the treatment laser beam or aiming light beam according to the preset time determined based on each setting of the irradiation conditions. In this way, the irradiation of the treatment laser beam or aiming light beam can be carried out according to the preset irradiation conditions such as an irradiation form, an irradiation size, and the like.

It is to be noted that if the treatment laser beam, having strong intensity, is allowed to unlimitedly irradiate the inside of the hand piece unit by the rotation of a polygon mirror, it may break the hand piece unit. To avoid it, the rotation of the polygon mirror, i.e., the driven mirror 12a in the embodiment is controlled to reflect the laser beam to irradiate a predetermined area on the inside of the hand piece unit, i.e., on the driven mirror 12b.

For another manner to control the irradiation of treatment laser or aiming light to an irradiation area, a turn-angle sensor may be used. This turn-angle sensor constantly detects the rotation angle of the drive motor 13a and transmits detection signals to the controller, which operates to start the irradiation of a treatment laser beam or aiming light beam after the rotation angle of the drive motor 13a (the driven mirror 12a), considering the rotation speed and direction of the drive motor 13a, reaches the angle at which the driven mirror 12a can deflect the treatment laser beam or aiming light beam to irradiate a desired position (area) on the driven mirror 12b. The controller operates to stop the irradiation of the treatment laser beam or aiming light beam in accordance with the preset time determined based on the rotating speed and direction of the drive motor 13a and the irradiation conditions such as the irradiation area form, the irradiation area size, and the like.

Alternatively, the controller may operate to stop the irradiation of the treatment laser beam or aiming light beam when the rotation angle of the drive motor 13a (the driven mirror 12a), considering the rotation speed and direction of the drive motor 13a, becomes outside the angle at which the driven mirror 12a can deflect the treatment laser beam or aiming light beam to the desired position (area) on the driven mirror 12b.

For a further different manner, a stepping motor may be used for the drive motor 13a, which operates at the rotation angle in proportion to the number of input pulses. With the stepping motor, the controller can operate the irradiation of the treatment laser beam or aiming light beam based on the number of input pulses corresponding to the rotation angle which meets the settings of the irradiation conditions such as the form or size of the irradiation area.

The hand-piece head section 11 is made of transparent resin in a generally cone shape to cover the laser scanning area at its bottom, so that an operator can view from outside the treatment area and irradiation area covered by the hand piece head section 11. The hand piece head section 11 has in its side wall the cuts for fume outlets 15 through which the fumes generated by the laser irradiation on the treatment area are evacuated from the hand piece head section 11. In operation, a jet of air produced by an air purging pump in the laser unit 1 is conducted through the connector 5 and the air tube 6 to an air jet port 16 located near the top of the hand piece head section 11, so that an air jet introduced into the head section 11 dispels fumes through the fume outlets 15. Incidentally, the bottom of hand piece head section 11 has the size which can secure the scanning area of the laser beam for the treatment.

Figure 4:
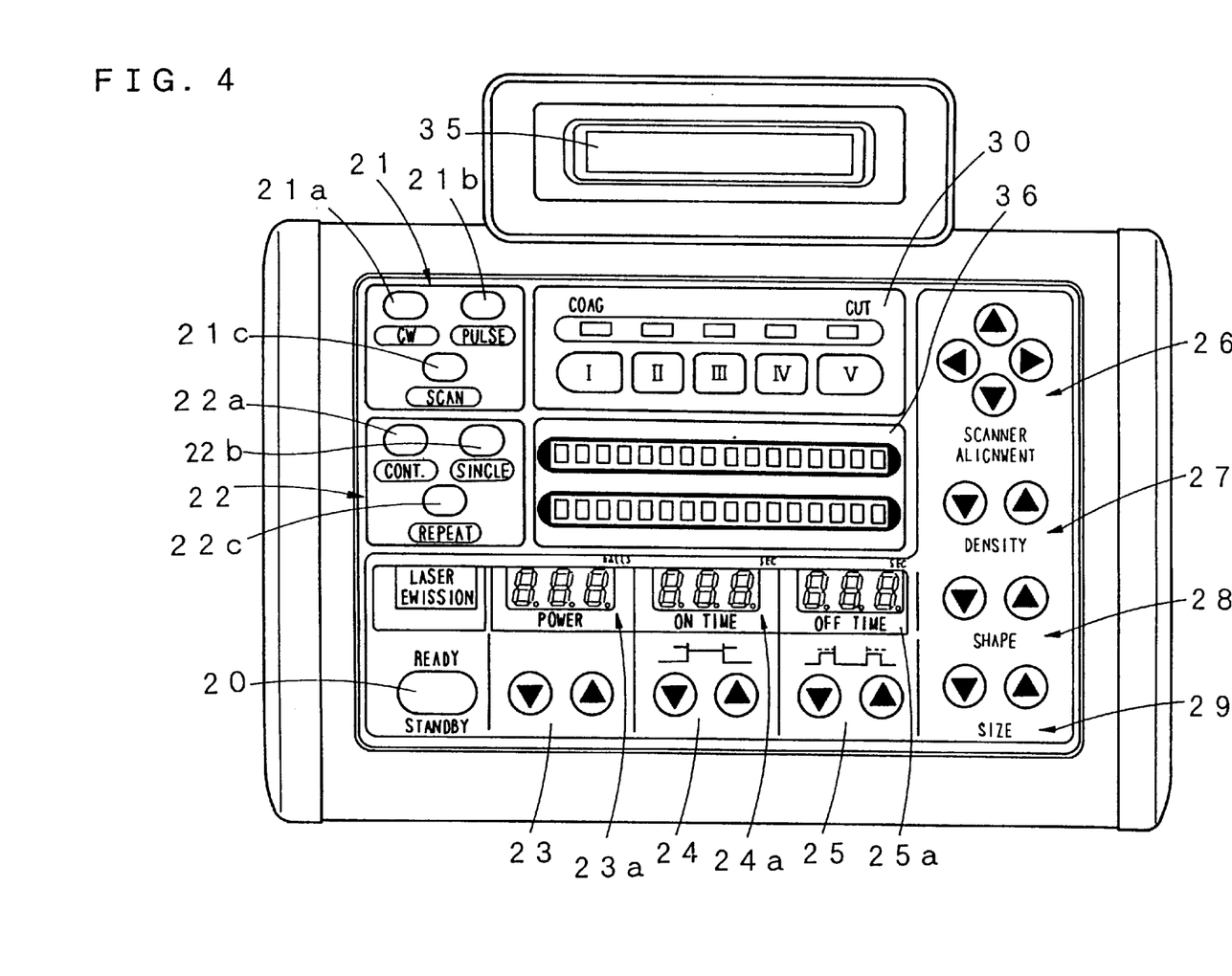
FIG. 4 is a top view of a control panel of the laser treatment apparatus.

Instead of the two fume outlets 15 formed in the side wall of the hand piece head section 11, more than two fume outlets may be provided. In addition, the hand piece head section 11 may be designed so that it is put into contact at three portions of the bottom with the patient's body around the treatment area, whereby the operator can stably hold the hand piece unit 3. FIG. 4 shows a top view of the control panel 7, which includes the following keys.

A READY/STANDBY key 20 is used by the operator to switch the apparatus between the ready (laser irradiation enabled) state and the standby (wait) state. In the ready state, the apparatus can irradiate a laser beam in response to the trigger signal from the foot switch 8, whereas in the standby state, the trigger signal is locked so as to preclude the laser irradiation caused by the erroneous input of the trigger signal at the setting of conditions. Mode select keys 21 include a CW mode (for continuous emission) select key 21a, a pulse mode (for pulsative emission) select key 21b, and a scan mode select key 21c, which are used by the operator to designate the CW mode, pulse mode, or scan mode according to the treatment conditions. When the operator selects a mode, the sign below the relevant key lights up to indicate the established mode.

Irradiation pattern select keys 22 include a CONT (continuous irradiation) pattern select key 22a, a SINGLE (one-shot irradiation) pattern select key 22b, and a REPEAT (repetitive irradiation) pattern select key 22c. When the operator selects a pattern, the sign below the relevant key lights up to indicate the selected pattern.

Irradiation power setting keys 23 including UP key and DOWN key are used to set the power level of the treatment laser beam, with the setup power level being displayed in the display window 23a. In the present embodiment, the range of setting is from 0.1 to 40W in the case of CW mode (the maximum value differs depending on the mode) in 0.1W step in the 0.1–1W range and in 1W step in the 1–40W range.

ON-TIME setting keys 24 including UP key and DOWN key are used for the operation with the single pattern or repeat pattern in CW mode or pulse mode to set the duration of laser irradiation, with the setup duration being displayed in a display window 24a. In the present embodiment, the range of setting is from 0.02 to 5 sec. in 0.02 sec. step in the 0.02–0.1 sec., in 0.1 sec. step in the 0.1–1 sec., and 1 sec. step in the 1–5 sec.

OFF-TIME setting keys 25 including UP key and DOWN key are used for the operation with the repeat pattern in CW mode, pulse mode or scan mode to set the duration of a halt of laser irradiation, with the setup duration being displayed in a display window 25a. The range and step of setting are identical to those of the on-time setting keys 24.

Alignment keys 26 are used for the fine adjustment of irradiation position in scan mode. With operation of the alignment keys 26, the operator can move the position of irradiation area without the need of moving the hand piece head section 11.

Irradiation density setting keys 27 including UP key and DOWN key are used to set the laser irradiation density in scan mode, with the setup density being displayed in a display window 35.

Irradiation form setting keys 28 including UP key and DOWN key are used in scan mode to select a shape of laser irradiation area, in the present embodiment, from among several preset shapes such as triangle, square, hexagon, etc. The selected form is displayed in the display window 35.

Irradiation size select keys 29 including UP key and DOWN key are used in scan mode to select the size of laser irradiation area. The selected size is displayed in the display window 35. Pulse interval select keys 30 are used in pulse mode to select a laser pulse irradiation interval from among five values in the present embodiment.

The display window 35 displays the information in scan mode. A display window 36 displays the information on error messages and machine states.

Next, the operation of the laser treatment apparatus arranged as described above will be explained with reference to FIG. 5, which shows the control system and the optical system of the apparatus. Here, the laser irradiation with single pattern for one scanning operation in the scan mode is described.

Figure 5:
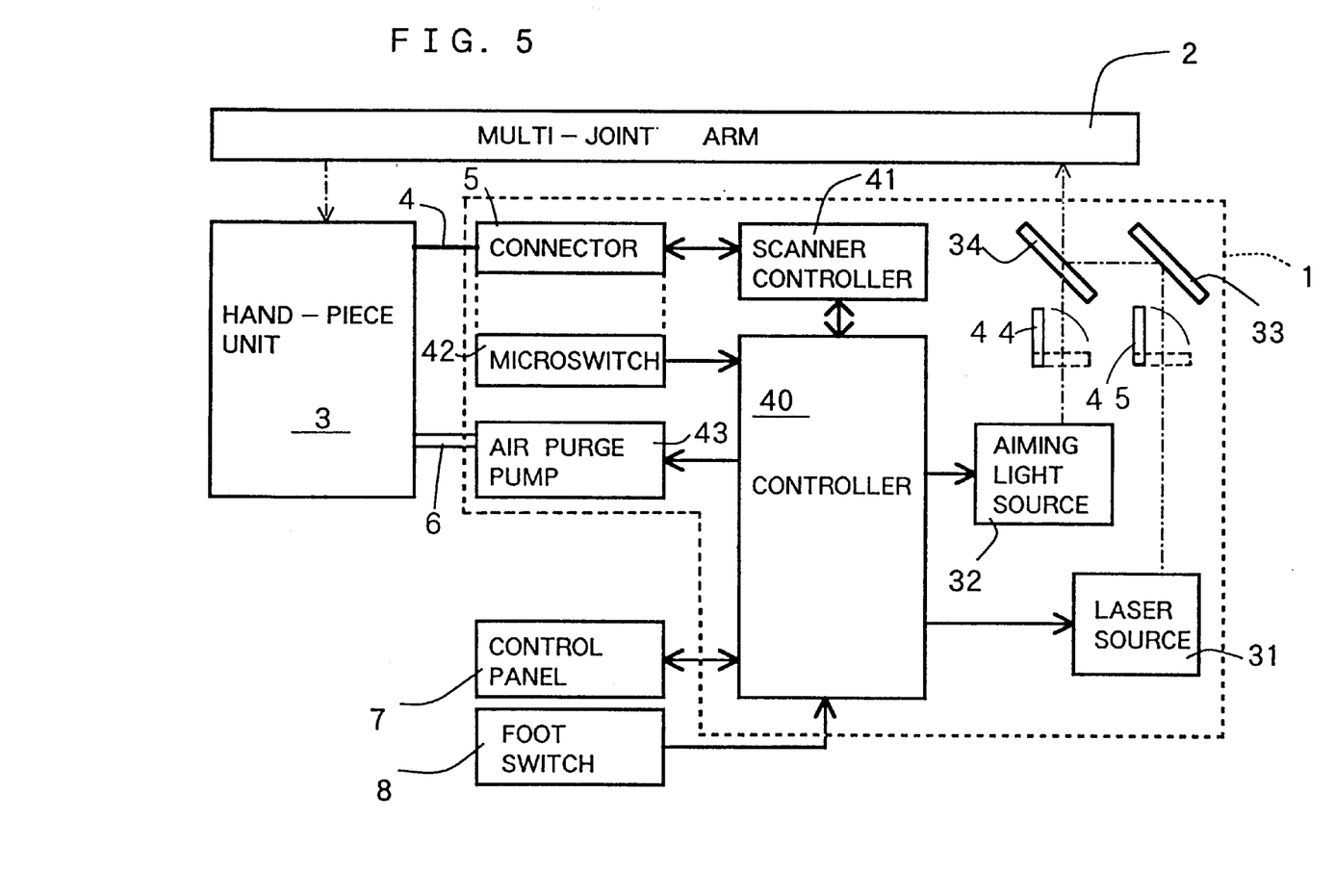
FIG. 5 is a block diagram showing a control system and an optical system of the laser treatment apparatus.

When the apparatus is turned on, a controller 40 carries out the self-diagnostic check for each section, displaying a message of "on self-diagnostic check" in the display 36. Upon completion of the checks, the controller 40 automatically enters the standby state, causing the control panel 7 to light up the STANDBY sign below key 20 and display a message of "standby state" in the display window 36.

The apparatus checks the connection of the cable 4 to the connector 5 by means of a microswitch 42 in the self-diagnostic checks (or during the power-on period), and if disconnection is detected, the controller 40 cuts off the power supply to a scanner controller 41, thereby preventing the malfunctioning of the apparatus.

The operator confirms the apparatus in standby state by viewing the display on the control panel 7, and brings the entire bottom plane of the hand piece head section 11 in contact with the patient's body so that the portion to be treated is entirely covered by the hand piece head section 11. In case of a scanning operation by the treatment laser beam, the operator pushes in advance the scan mode select key 21c on the control panel 7 to set the scan mode for laser irradiation. While viewing the irradiation position of the aiming light emitted from the aiming light source 32 and irradiated through the hand piece unit 3 onto the treatment area, the operator pushes the keys on the control panel 7 to set irradiation conditions, i.e., the irradiation pattern, the form and size of irradiation area according to the treatment. The operator also carries out the fine adjustment of irradiation position by using the alignment keys 26.

The setup signal of each irradiation condition is transmitted through the controller 40 to the scanner controller 41, which sends a drive signal in accordance with the irradiation conditions to the scanner section 10, thereby to operate on the drive motor 13a to rotate the driven mirror 12a at a predetermined speed in a predetermined direction, and operate on the drive motor 13b to swing the driven mirror 12b at a predetermined step (speed) to a desired angle.

Figure 6A:
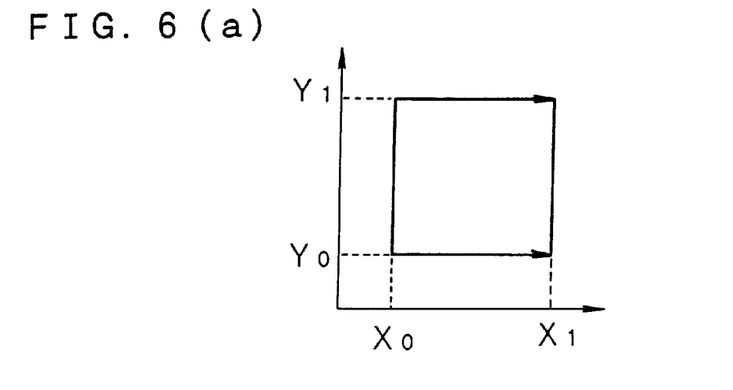
FIG. 6 is a graph used to explain the scanning irradiation manner of an aiming light.
Figure 6B:
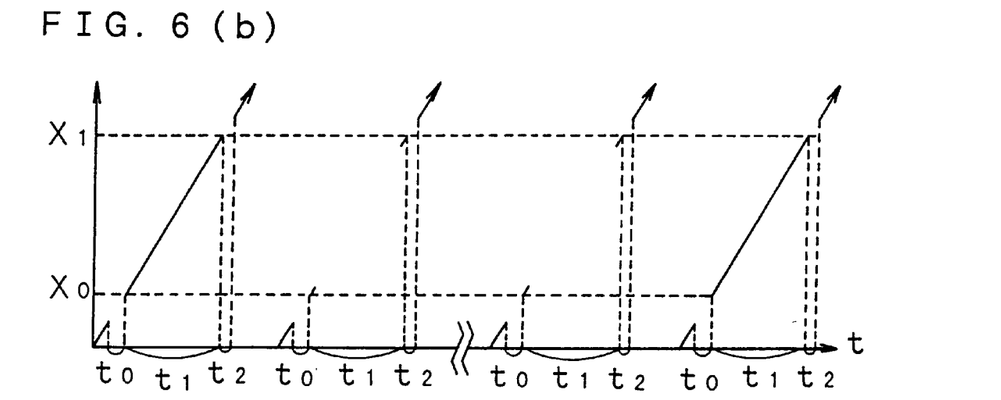
Figure 6C:
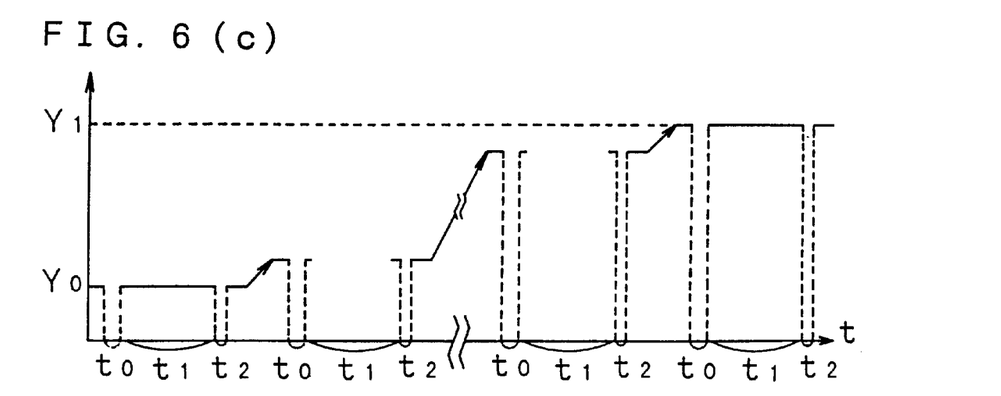

Assuming that the selected form of irradiation area is, for example, a square shape as shown in FIG. 6(a), the aiming light beam is allowed by the rotation of the driven mirror 12a to scan the irradiation area in the X-direction as shown in FIG. 6(b) while it is allowed by the swing of the driven mirror 12b to scan the irradiation area in the Y-direction as shown in FIG. 6(c). At this time, the irradiation of aiming light beam is controlled along the lapse of time, i.e., based on the time $t_0$ between the detection of the aiming light beam by the sensor 17 and the start of irradiation of the aiming light beam to the position $X_0$ (during which the aiming light is interrupted by a shutter 44), the time $t_1$ during which the irradiation of aiming light beam is implemented from the position $X_0$ to $X_1$ (the irradiation of aiming light beam is carried out at only the start and end of the time $t_1$ in the area excepting the positions $Y_0$ and $Y_1$), and the time $t_2$ between the halt of irradiation after the end of irradiation to the position $X_1$ and the restart of irradiation (during which the aiming light beam is interrupted by the shutter 44). Those times $t_0$, $t_1$, and $t_2$ are previously calculated and determined based on each setting irradiation condition. When the settings of the irradiation form and size are changed, the irradiation of the aiming light beam is controlled along the times $t_0$, $t_1$, and $t_2$ set based on the changed settings, so that the irradiation of the aiming light beam is controlled in accordance with the current settings of the irradiation conditions. It is to be noted that the area from the position $Y_0$ to $Y_1$ is controlled according to the width of a swing angle of the driven mirror 12b, the width being determined based on the setting irradiation conditions.

Instead of the sensor 17 which detects the aiming light beam to control the irradiation thereof along a lapse of time, other methods for controlling the irradiation of the aiming light beam may be used as mentioned above. There may be used, for example, a turn-angle detector which constantly detects the rotation angle of the drive motor 13a to control the irradiation of the aiming light after the rotation angle reaches a predetermined angle, or a stepping motor for the drive motor 13a to control the aiming light irradiation based on the number of input pulses.

Since the hand piece head section 11 is made of transparent resin, the operator can easily view the irradiation position and irradiation area on the treatment area even if it is entirely covered by the hand piece head section 11 with its bottom in contact with the patient's skin. The hand piece head section 11, having a general cone shape, is put into uniform contact at its entire bottom plane with the patient's skin, so that the operator can hold stably the hand piece unit 3 on the patient's body with the stable distance between the laser irradiation port of the scanner section 10 and the treatment area. Furthermore, the hand piece head section 11 is in contact with a relatively large area of the patient's skin, so that the force of pressing the skin is dispersed, preventing deformation of the skin around the treatment area, thus enabling the provision of constant stable irradiation distance. Upon definition of the irradiation area based on the setting irradiation conditions and the observation of the aiming light, the operator pushes the READY/STANDBY key 20 to switch the apparatus into a ready state. In this state, the operator depresses the foot switch 8 to generate a trigger signal.

The trigger signal from the foot switch 8 is transmitted via the controller 40 to the scanner controller 41. In response to the trigger signal, the scanner controller 41 sends the drive signals of the form and size of irradiation area, etc. in accordance with the settings on the control panel 7 to the scanner section 10 thereby to operate on the drive motors 13a and 13b. The drive motor 13a rotates the driven mirror 12a at a predetermined speed in a predetermined direction, whereas the drive motor 13b swings the driven mirror 12b at a predetermined step (speed) to a desired angle.

The controller 40 which has received the trigger signal from the foot switch 8 sends the drive signal in accordance with the settings on the control panel 7 to cause the laser source 31 to emit a treatment laser beam. The treatment laser beam emitted from the laser source 31 is reflected by the mirror 33 and the dichroic mirror 34, aligned coaxially to the aiming light beam from the aiming light source 32, and introduced to the multi-joint arm section 2. The coaxial treatment laser beam and aiming light beam are reflected by the mirrors located at the joints of the arm section 2 and led to the hand piece unit 3.

Figure 7:
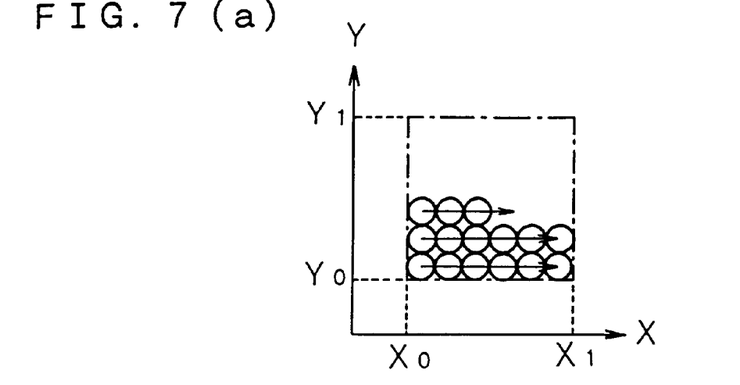
FIG. 7 is a graph used to explain the scanning irradiation manner of a treatment laser beam.

Succeedingly, in the case of the form and size of irradiation area being set in a square shape shown in FIG. 7(a), for example, the treatment laser beam and aiming light beam led to the hand piece unit 3 are allowed to scan in the X-direction as shown in FIG. 7(b) by the rotation of the driven mirror 12a and also in the Y-direction as shown in FIG. 7(c) by the swing of the driven mirror 12b. During the scanning, the laser irradiation is controlled along the lapse of time, i.e., based on the time $t_3$ between the detection of the aiming light by the sensor 17 and the start of laser irradiation to the position $X_0$ on the irradiation area. The time $t_3$ is preset by calculation in accordance with the setting irradiation conditions. The irradiation duration of the treatment laser beam (the number of irradiation operations) is also determined in advance based on each of the setting irradiation conditions.

Detecting the scanning irradiation of the aiming light beam in the X-direction by the driven mirror 12a, the sensor 17 transmits a signal to the controller 40. After a lapse of the time $t_3$, the controller 40, which has interrupted the laser beam by the shutter 45, restarts the laser irradiation, and interrupts the laser beam again after it irradiates a designated area or position in the X-direction. Before the aiming light shifted by the rotation of the driven mirror 12a is detected again by the sensor 17 or before the laser irradiation is restarted, the driven mirror 12b is swung to the next designated angle to move the laser beam in the Y-direction. Upon detection of the aiming light by the sensor 17 and after a lapse of time $t_3$, the controller 40 restarts the laser scanning irradiation in the X-direction caused by the driven mirror 12a.

As mentioned above, the driven mirrors 12a and 12b are driven by the drive motors 13a and 13b to control the laser irradiation along the lapse of time, so that the treatment laser beam can be allowed to scan the treatment area in the X- and Y- directions in accordance with the desired form and size of irradiation area. Instead of the sensor 17 which detects the aiming light beam to control the laser irradiation along a lapse of time, other methods for controlling the laser irradiation may be used as mentioned above. There may be used, for example, a turn-angle detector which constantly detects the rotation angle of the drive motor 13a to control the laser irradiation after the rotation angle reaches a predetermined angle, or a stepping motor for the drive motor 13a to control the laser irradiation based on the number of input pulses.

Figure 8A:
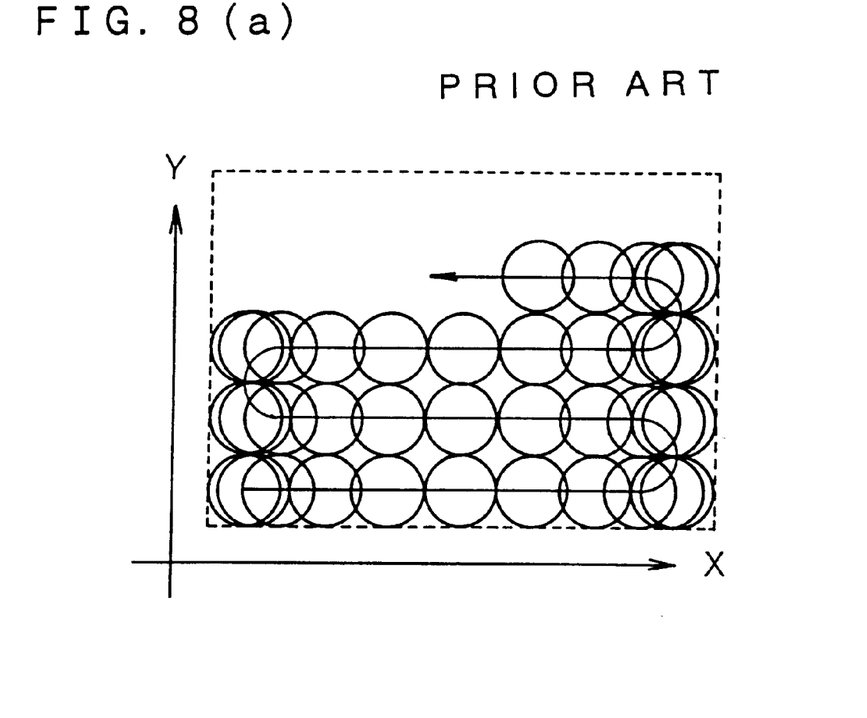
Figure 8B:
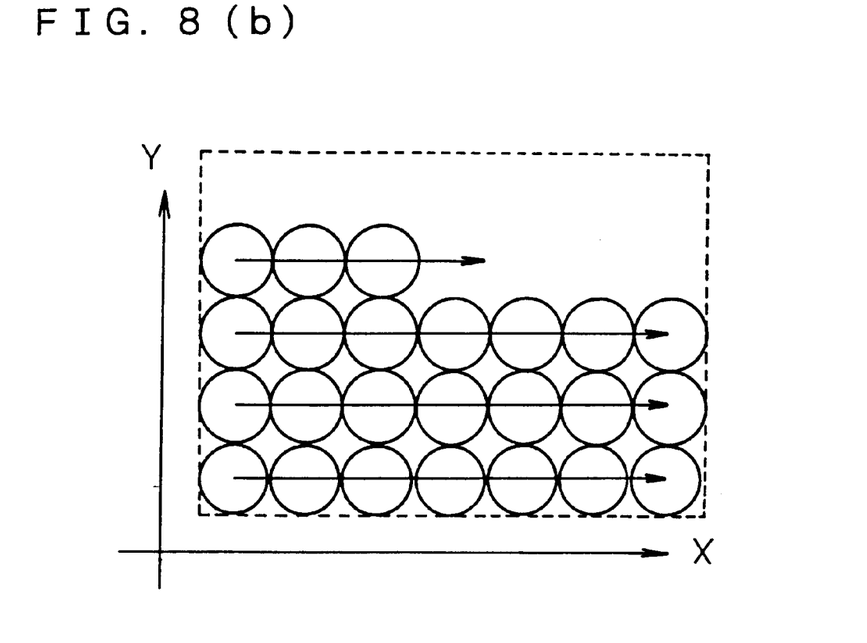

Meanwhile, FIG. 8(a) shows a scanning manner of a treatment laser beam in a conventional laser treatment apparatus, which uses swinging galvano-mirrors for the driven mirrors and motors for both X- and Y- directions. Such the apparatus would cause the over-irradiation of treatment laser on a specified part of the irradiation area due to a difference in swing speed of the mirrors. Concretely, the swing speed is reduced before and after the driven mirror is inclined to the maximum angle at the start and end of scanning in the X-direction, so that continuous laser emission or pulsative laser emission at constant intervals may cause much laser irradiation on the specified part which corresponds to the slow swing speed of the driven mirror. To prevent such the over-irradiation, the apparatus according to the present invention is designed so that the driven mirror 12a is rotated in a predetermined direction to implement one-way scanning laser irradiation in the X-direction, resulting in the laser irradiation with a uniform energy through the start to end positions in the X-direction as shown in FIG. 8(b).

During the laser irradiation, the controller 40 activates the air purging pump 43 to feed air into the hand piece head section 11, thereby expelling fumes created by laser irradiation through the fume outlets 15.

As described above, in case that the scanning hand piece unit 3 is connected to the apparatus, the scanner controller 41 always transmits/receives signals to/from the hand piece unit 3 through the connector 5. If the scanner controller 41 receives no feedback signal from the hand piece unit 3, the controller 40 causes the display window 36 to display an error message. In case of only disconnection of the cable 4 to the connector 5, which is detected by means of the microswitch 42, the controller 40 cuts off the power supply to the scanner controller 41 and causes the display window 36 to display a message to indicate the disconnection of the scanning hand piece unit 3. Accordingly, the operator can recognize the connection error between the hand piece unit 3 and the scanner controller 41 or the disconnection of the cable 4 to the connector 5 to take an appropriate action with respect to the apparatus. Instead of the scanning hand piece unit 3, in case of the use a hand piece unit not for scanning operation, needing no operation of the scanner controller 41, the controller 40 cuts off the power supply to the scanner controller 41 in response to the information on the disconnection of the cable 4 to the connector 5. This can prevent the apparatus from entering in a scan mode even if the operator pushes the scan mode select key 21*c* on the control panel 7 by error, thus preventing the malfunctioning of the apparatus.

Detecting the end of scanning by receiving the feedback signal from the hand piece unit 3, the scanner controller 41 stops the drive motors 13*a* and 13*b*, while it sends the scanning end signal to the controller 40. Based on the scanning end signal, the controller 40 operates on a safety shutter and the like (not shown) to interrupt the treatment laser beam from the laser source 31.

In this way, with the single pattern being selected, even if the trigger signal from the foot switch 8 retains active, the laser irradiation and scanning operation terminate on completion of one scanning operation.

The present invention may be embodied in other specific forms without departing from the spirit or essential characteristics thereof. For instance, although a polygon mirror is used for the driven mirror 12*a* in the above embodiment, an alternative design is the use of a mirror (reflector) having a reflecting surface with high smoothness may be used. Although the above embodiment uses a DC servo-motor used for the driven mirror 12*b*, an alternative design is the use of a motor which makes a continuous one-way rotation, for example, a stepping motor and the like.

Although the above embodiment uses the rotating mirror and the motor therefor (e.g., a polygon mirror and a DC servo-motor) to move the laser beam in the X-direction and the swing mirror and the motor therefor (e.g., a galvano-mirror) to move the laser beam in the Y-direction, these mirrors and motors may be reversely used, namely, the swing mirror and the motor therefor are used to move the laser beam in the X-direction and the rotating mirror and the motor therefor are used to move the laser beam in the Y-direction. Also, the rotating mirrors and motors may be used to move the laser beam in both the X-direction and Y-direction.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus which irradiates an area of treatment by a laser beam produced by a treatment laser source, the apparatus comprising:

irradiation condition setting means for setting irradiation conditions of the laser beam, including an irradiation area;

laser scanning means which is provided with a plurality of reflectors including at least a first reflector which is continuously rotated in a predetermined direction by a motor, and which performs a laser two-dimensional scanning on the treatment area;

scanning control means which controls the continuous operation of the laser scanning means based on the irradiation conditions set by the irradiation condition setting means; and by irradiation control means which controls the irradiation by the laser beam based on the irradiation conditions and stops the laser irradiation of the treatment area in the interval from the termination of one scan of the treatment area by the first reflector rotating in the predetermined direction to the beginning of a next scan.

2. A laser treatment apparatus according to claim 1, wherein the first reflector which is rotated in the predetermined direction comprises a polygon mirror.

3. A laser treatment apparatus according to claim 1, further comprising:

aiming light generating means for generating an aiming light for guiding the laser beam to the treatment area; and light detecting means which detects the aiming light;

and the irradiation control means controls the irradiation by the laser beam depending on the result of the detection by the light detecting means.

4. A laser treatment apparatus according to claim 1, further comprising turn-angle detecting means which detects a turn angle of the motor rotated to rotate the first reflector in the predetermined direction, and the irradiation control means controls the irradiation by the laser beam depending on the result of detection by the turn-angle detecting means.

5. A laser treatment apparatus according to claim 1, wherein the motor comprises a stepping motor, and the irradiation control means controls the irradiation by the laser beam depending on the number of pulses input to the stepping motor.

6. A laser treatment apparatus according to claim 1, wherein the irradiation control means comprises a shutter for stopping the laser beam.

* * * * *

UNITED STATES PATENT AND TRADEMARK OFFICE
CERTIFICATE OF CORRECTION

PATENT NO.: 5,971,978

DATED: October 26, 1999

INVENTOR(S): Hideo Mukai

It is certified that an error appears in the above-identified patent and that said Letters Patent is hereby corrected as shown below:

Claim 1, col. 10, line 18, delete "by".

Signed and Sealed this

Fourth Day of April, 2000

Attest:

Attesting Officer

Q. TODD DICKINSON

Director of Patents and Trademarks